United States Patent
Whitley et al.

(10) Patent No.: US 6,764,675 B1
(45) Date of Patent: Jul. 20, 2004

(54) HERPES SIMPLEX VIRUS EXPRESSING FOREIGN GENES AND METHOD FOR TREATING CANCERS THEREWITH

(75) Inventors: Richard J. Whitley, Birmingham, AL (US); James MacDowell Markert, Birmingham, AL (US); George Yancey Gillespie, Birmingham, AL (US); Jacqueline Ness Parker, Brimingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/009,972
(22) PCT Filed: Jun. 8, 2000
(86) PCT No.: PCT/US00/40165
§ 371 (c)(1), (2), (4) Date: Feb. 14, 2002
(87) PCT Pub. No.: WO00/75292
PCT Pub. Date: Dec. 14, 2000

Related U.S. Application Data

(60) Provisional application No. 60/144,314, filed on Jul. 16, 1999, and provisional application No. 60/138,173, filed on Jun. 8, 1999.

(51) Int. Cl.[7] .............................................. A01N 63/00
(52) U.S. Cl. ..................... 424/93.2; 514/44; 435/320.1; 435/455; 435/456
(58) Field of Search .......................... 424/93.2; 514/44; 435/320.1, 455, 456

(56) References Cited

U.S. PATENT DOCUMENTS

| | | | |
|---|---|---|---|
| 5,641,651 A | 6/1997 | Roizman | 435/69.1 |
| 5,714,153 A | 2/1998 | Roizman | 424/231.1 |
| 5,804,413 A * | 9/1998 | DeLuca | 435/69.1 |
| 5,846,707 A | 12/1998 | Roizman | 435/5 |
| 5,849,572 A | 12/1998 | Glorioso et al. | 435/320.1 |
| 6,090,562 A | 7/2000 | Bridgham et al. | 435/6 |
| 6,096,869 A | 8/2000 | Stanley et al. | 530/351 |
| 6,287,557 B1 * | 9/2001 | Boursnell et al. | 424/93.2 |
| 6,602,499 B1 * | 8/2003 | Chiocca et al. | 423/93.2 |
| 2002/0098170 A1 * | 7/2002 | Wechsler et al. | 424/93.21 |

FOREIGN PATENT DOCUMENTS

| | | |
|---|---|---|
| WO | WO 96/26267 A1 * | 8/1996 |
| WO | WO 98/42855 | 10/1998 |
| WO | WO 99/07394 | 2/1999 |

OTHER PUBLICATIONS

Todryk et al., "Disabled infectious single–cycle herpes simplex virus as an oncolytic vector for immunotherapy of colorectal cancer," Hum. Gene Ther. 10(17): 2757–2768, Nov. 20, 1999.*

Andreansky et al., *"Treatment of intracaranial gliomas in immunocompetent mice using herpes simplex viruses that express* murine interleukins," Gene Ther. 5 (1): 121–130, Jan. 1998.*

Masahiro Toda et al. "In Situ Vaccination: An IL–12 Defective Vector/Replication–Component Herpes Simplex Virus Combination Induces Local and Systemic Antitumor Activity" The Journal of Immunology 160:4457–4464 (1998).

* cited by examiner

*Primary Examiner*—Scott D. Priebe
(74) *Attorney, Agent, or Firm*—Gifford, Krass, Groh, Sprinkle, Anderson & Citkowski, P.C.

(57) ABSTRACT

An anti-cancer pharmaceutical composition includes a herpes simplex virus (HSV) vector into which a nucleic acid sequence encoding an anti-cancer agent selected from interleukin-12, GM-CSF, and CD has been inserted. A method of treatment of a patient suffering from cancer includes administering to the patient the anti-tumor pharmaceutical composition including an HSV vector having a nucleic acid sequence encoding an anti-cancer agent selected from interleukin-12, GM-CSF, and CD inserted therein.

5 Claims, 6 Drawing Sheets

M004

M012

HERPES SIMPLEX VIRUS EXPRESSING FOREIGN GENES AND METHOD FOR TREATING CANCERS THEREWITH

REFERENCE TO RELATED APPLICATIONS

This application is the U.S. National phase of PCT application Ser. No. PCT/US00/40165, filed Jun. 8, 2000, and published under PCT Article 21(2) in English, which claims priority from U.S. Provisional Patent Applications Serial No. 60/138,173, filed Jun. 8, 1999, and Ser. No. 60/144,314, filed Jul. 16, 1999.

GRANT REFERENCE

The research carried out in connection with this invention was supported under a contract (NO1-AI-62554) with the Antiviral Research Branch of the National Institute of Allergy and Infectious Diseases (NIAID), Program Project Grants (PO1 AI 24009; PO1 CA 71933), and the National Institute for Neurologic Disorders and Stroke Mentored Clinical Scientist Development Award (1K08NSO1942).

FIELD OF THE INVENTION

The present invention generally relates to modified herpes simplex virus (HSV) vectors and their use for the treatment of tumors. In particular, the present invention relates to HSV expressing a foreign gene such as interleukin 12, granulocyte macrophage colony stimulating factor (GM-CSF), or cytosine deaminase (CD) and a method for treating cancers therewith.

BACKGROUND OF THE INVENTION

Eradication of malignancies arising in the brain has proven to be a formidable task. As an example, gliomas, the most common primary brain tumor, are almost always fatal despite aggressive surgical resection, radiotherapy and chemotherapy; the overall five year survival rate for glioblastoma (GBM), the most malignant glioma, is less than 5.5% and the median survival is approximately one year.

Because of poor survival of patients with GBM and other brain malignancies, novel therapeutic approaches, most notably viral and gene therapy, have been investigated (for reviews, see Markert et al. (1999) *Rev. Med. Virology* in press; Cobbs et al. (1999) *Persp. Neurolog. Surg.* in press; Andreansky et al. (1996) *Proc. Natl. Acad. Sci. USA* 93, 11313–11318). The efficacy of using neuroattenuated replication-competent herpes simplex viruses (HSV) for treatment of primary brain tumors is known. These viruses typically contain one or more mutations within the viral genome, including thymidine kinase (tk) (Martuza et al. (1991) *Science* 252, 854–856), ribonucleotide reductase (Mineta et al. (1995) *Num. Gene Ther.* 1, 938–943; Kramm et al. (1997) *Hum. Gene Ther.* 8, 2057–2068), UTPase (Pyles et al. (1997) *Hum. Gene Ther.* 8, 533–544) or $\gamma_1 34.5$ (Markert et al. (1993) *Neurosurg.* 32, 597–603; Chambers et al. (1995) *Proc. Natl. Acad. Sci. USA* 92, 1411–1415). Moderate increases in long-term survival for engineered HSV-treated versus untreated animals have been reported in both syngeneic and xenogeneic murine tumor models of GBM (Markert et al. (2000) *Rev. Med. Virology* 10, 17–30; Martuza et al. (1991) *Science* 252, 854–856; Markert et al. (1993) *Neurosurg.* 32, 597–603; Chambers et al. (1995) *Proc. Natl. Acad. Sci. USA* 92, 1411–1415; Mineta et al. (1994) *Gene Ther.* 1 Suppl 1:S78, S78; Andreansky et al. (1997) *Cancer Res.* 57, 1502–1509; Andreansky et al. (1998) *Gene Ther.* 5, 121–130; Kaplitt et al. (1994) *J. Neuro-Onc.* 6, 137–147; Yazaki et al. (1995) *Cancer Res.* 55, 4752–4756). In addition, Phase I studies in humans with malignant glioma suggest that a multiply mutated HSV (G207) at doses up to $3 \times 10^9$ pfu is safe for intracranial inoculation (Markert, J M; Medlock, M D; Rabkin S D; Gillespie, G Y; Feigenbaum, F; Hunter, W D; Todo, T; Tornatore, C; and Martuza, R L, unpublished data.

Despite these advantages, it seems likely that multiple modalities of therapy will be necessary to eradicate malignant tumors of the central nervous system (CNS) as well as those originating outside the brain. To increase the efficacy of anti-neoplastic therapy, Applicants studied conditionally replicating $\gamma_1 34.5^-$ mutants as vectors for gene therapy. These vectors retain direct oncolytic effects for tumor cells, and, additionally, express foreign genes designed to augment their anti-tumor effects. Initially, conditionally replicating mutants expressing interleukin 4 (IL-4) and IL-10 were studied (Andreansky et al. (1998) *Gene Ther.* 5, 121–130). These viruses were evaluated in an orthotopic model of murine glioblastoma utilizing syngeneic GL-261 tumors implanted into immunocompetent C57BL/6 mice. In this model, treatment with IL-4 expressing HSV increased survival over treatment with HSV alone, suggesting that cytokine gene therapy may mediate enhanced tumor-specific killing. IL-4 gene therapy has been shown to enhance anti-glioma effects in several gene therapy models (Okada et al. (1999) *Gene Ther.* 6, 219–226; Wei et al. (1998) *J. Neurovirol.* 4, 237–241; Benedetti et al. (1997) *Num. Gene Ther.* 8, 1345–1353). Such effects are $T_H$-2-mediated and have been attributed to CD4$^+$ lymphocytes and other effector cells such as eosinophils (Tseng et al. (1997) *J. Immunother.* 20, 334–342). While IL-4 was effective in these animal models, generation of a $T_H$-1 response, including induction of a memory response against tumor cells, need to have a more durable anti-tumor effect.

Therefore, Applicants constructed a virus expressing a cytokine with increased potential for a tumor-specific response. Interleukin-12 (IL-12) is a cytokine with potent anti-tumor properties. It is produced by antigen-presenting cells including B lymphocytes, dendritic cells, and monocytes and acts to enhance the cytolytic activity of natural killer (NK) and cytotoxic T lymphocytes (CTL) and the development of a $T_H$-1-type immune response (Caruso et al. (1996) *Proc. Natl. Acad. Sci. USA* 93, 11302–11306; Bramson et al. (1996) *Num. Gene Ther.* 7, 1995–2002; Kishima et al. (1998) *Brit. J. of Cancer* 78, 446–453; Meko et al. (1996) *Surgery* 120, 274–283; Nishimura et al. (1996) *Ann. NY Acad. Sci.* 795, 375–378; Tahara et al. (1995) *Num. Gene Ther.* 6, 1607–1624; Tahara et al. (1995) *Gene Ther.* 2, 96–106). IL-12 also possesses anti-angiogenic properties, which may represent a second potential mechanism for its anti-tumor activity (Majewski et al. (1996) *J. Invest. Derm.* 106, 1114–1118; Kerbel et al. (1995) *J. Natl. Cancer Inst.* 87, 557–586). IL-12 has been demonstrated to produce anti-glioma immune activity in two different rodent models (Toda et al. (1998) *J. Immunol.* 160, 4457–4464; Kikuchi et al. (1999) *Cancer Let.* 135, 47–51). While experimental models utilizing IL-12 for gene therapy have been promising, none have utilized IL-12 expressed from a replication-competent vector (Caruso et al. (1996) *Proc. Natl. Acad. Sci. USA* 93, 11302–11306; Toda et al. (1998) *J. Immunol.* 160, 4457–4464; Rakhmilevich et al. (1997) *Num. Gene Ther.* 8, 1303–1311; Bramson et al. (1996) *Num. Gene Ther.* 7, 333–342; Tahara et al. (1995) *J. Immunol.* 154, 6466–6474; Myers et al. (1998) *Laryngoscope* 108, 261–268). Notably, Phase I human studies utilizing systemic IL-12 therapy have demonstrated toxicity of this cytokine, presumably due to its pleitrophic effects (Marshall et al. (1995) *Science* 1555).

Applicants have developed a conditionally replication-competent, $\gamma_1 34.5^-$ mutant, which expresses murine IL-12 (M002), for treatment of brain tumors that retains its ability to replicate in murine tumor cells, maintains its primary characteristic of direct tumor cell oncolysis, produces IL-12 at physiologically relevant amounts, allows for direct expression of the cytokine within the tumor cells after inoculation, increases survival of A/J mice, a murine strain more sensitive to HSV infection, implanted with a syngeneic immunocompetent clone of Neuro2A neuroblastoma tumor cells (median=52 days) after treatment with M002 versus treatment with the non-cytokine expressing parent virus, R3659 (median=24 days), and which significantly increases immune-related inflammatory infiltration by CD4+ T cells, macrophages and to a lesser extent, CD8+ cells in M002-treated tumors versus R3659-treated tumors in brain tissue.

Applicants have also developed conditionally replication competent, $\gamma_1 34.5$ mutants, which express murine GM-CSF (M004) and bacterial CD (M012) for treatment of brain tumors and other cancers.

There exists a need for an anti-tumor therapy, specifically for the treatment of tumors of the central nervous system such as brain tumors and other tumors originating outside the brain with cytokines, that overcomes the problems and disadvantages of previous therapies. The present invention fulfills this long-standing need in the art.

SUMMARY OF THE INVENTION

A method for treating a subject suffering from cancer includes administering a therapeutically effective amount of a herpes simplex virus (HSV) vector expressing a cytokine or other anti-cancer agent encoding nucleic acid sequence, such as coding for interleukin-12, into a subject inducing an anti-tumor response in the subject.

An anti-tumor pharmaceutical composition comprising a herpes simplex virus (HSV) vector comprising a nucleic acid sequence encoding for a compound selected from IL-12, GM-CSF, and CD operatively linked to a promoter, and a pharmaceutically acceptable carrier.

BRIEF DESCRIPTION OF THE DRAWINGS

The following detailed description is best understood with reference to the following drawings in which.

DETAILED DESCRIPTION OF THE INVENTION

It has now been found according to the present invention that malignant cancer cells can be treated with a genetically manipulated and/or modified herpes simplex virus, preferably type 1, (HSV-1) expressing a foreign gene, preferably an interleukin 12 (IL-12) gene in order to produce IL-12 constitutively with a target cell and can be used as an effective anti-tumor treatment. The engineered HSV-1 expressing IL-12 can also be used for the treatment of primary and metastatic central nervous system (CNS) tumors including, but not limited to meningiomas, pituitary adenomas, and acoustic neuromas, and specifically brain tumors including glioblastoma, malignant glioma, and low-grade glioma, either with or without cognate therapies such as chemotherapy and/or radiation therapy. Additionally, the engineered HSV-1 expressing IL-12 can be utilized in the treatment of non-CNS tumors including malignant melanoma, hepatocellular carcinoma, head and neck cancers, etc., both with and without cognate therapy. The engineered HSV-1 expressing IL-12 can also be utilized as a vaccine or vaccine adjuvant and also for the treatment of infectious diseases by stimulating the immune system.

Figure 6:
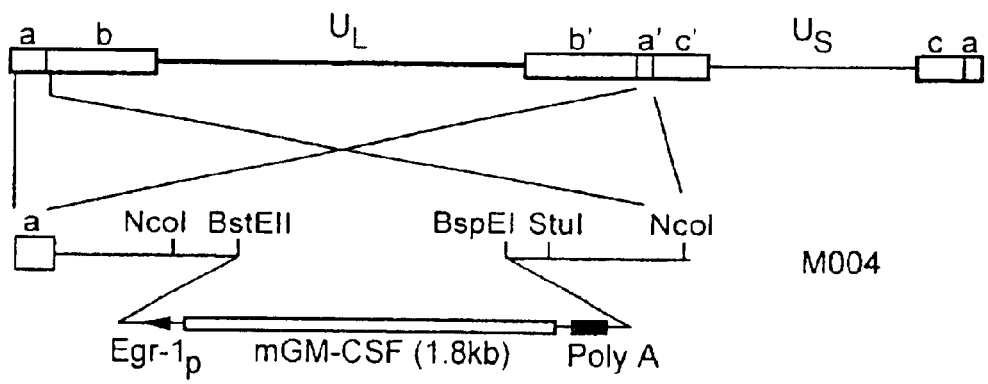
FIG. 6 is a schematic representation of GM-CSF-expressing HSV (M004).
Figure 7:
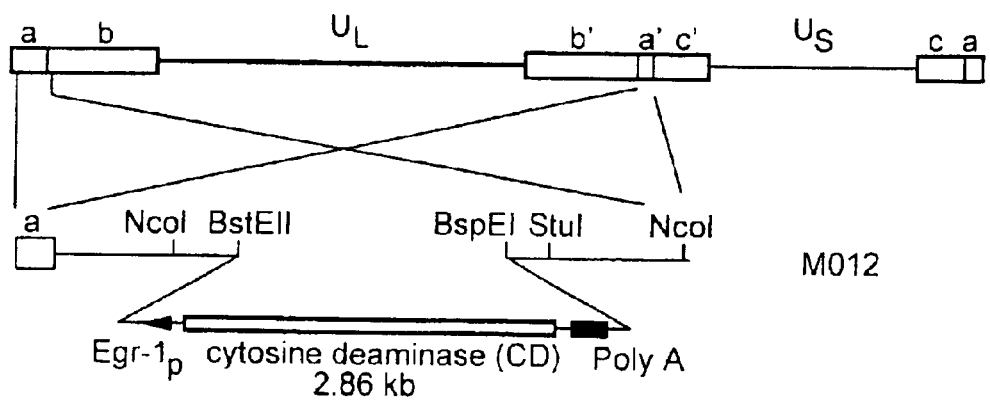
FIG. 7 is a schematic representation of cytosine deaminase-expressing HSV (M012).

The engineered HSV-1 vectors express a foreign gene including cytokines such as IL-12, granulocyte macrophage colony stimulating factor (GM-CSF), IL-16, IL-10, IL-4, or cytosine deaminase (CD) and are constructed by inserting the foreign gene, such as a gene encoding for cytokine or other anti-tumor/anti-cancer gene product, into the viral genome of HSV-1. The foreign gene is inserted into a region under the control of promoter-regulatory regions of the viral genome. Thus, the viral genome becomes a vector for the expression of the foreign gene in target cells (e.g., tumor cells). In the present invention, a nucleic acid sequence encoding for IL-12 (see FIG. 1) or some other anti-tumor/anti-cancer agent is placed under the transcriptional control of the murine early-growth response-1 promoter (Egr-1). It should be noted that while description is given herein for use of HSV-1 which is readily available to those of ordinary skill in the art, other herpes simplex viruses including HSV-2 can also be utilized in the present invention. See FIG. 6 for an HSV-1 vector expressing GM-CSF and see FIG. 7 for an HSV-1 vector expressing cytosine deaminase.

The HSV of the present invention is preferably a neuroattenuated, replication-competent HSV. The HSV-1 of the present invention includes a deletion in the $\gamma_1 34.5$ gene rendering the virus aneurovirulent.

As described below in the Experimental Section, biologically active murine IL-12 consists of heterodimer of the p40 and p35 subunits. The nucleic acid sequences encoding for the expression of the p35 and p40 subunits are separated by an internal ribosome entry site (IRES) and are inserted as a single expression cassette into HSV to form a recombinant HSV of the present invention. The HSV expresses the murine IL-12 via bicistronic expression of the p35 and p40 subunits separated by the IRES sequence. The IL-12 produced thereby is a self-assembling, heterodimeric, functionally active molecule in HSV-1. The cytokine can then exit the HSV and contact bystander cells and/or elicit and/or enhance the patient's or subject's immune response.

For the engineered HSV vector expressing GM-CSF it was shown by ELISA that significant production of GM-CSF was achieved in Vero cells and in the Neuro2A neuroblastoma cell line of A/J mouse origin. Neurotoxicity studies performed in highly sensitive A/J strain mice revealed that the GM-CSF virus was somewhat toxic at high doses, with an $LD_{50}$ of approximately $5 \times 10^6$ pfu. Intracranial studies demonstrated increased host survival in an intracranial syngeneic neuroblastoma murine model over mock-treated mice, although treatment with the GM-CSF virus at highest doses demonstrated toxicity.

For the engineered HSV vector expressing cytosine deaminase, cytosine deaminase activity was demonstrated in vitro by conversion of tritiated 5-fluorocytosine (5FC) to 5-fluorouracil (5FU). CD-expressing virus has been injected into U87MG human glioma cells intracranially xenografted into scid mice and 5FC was administered. The local expression of cytosine deaminase led to very localized tissue metabolism of drugs such as 5-fluorocytosine providing a local anti-tumor effect.

The present invention provides an anti-cancer or anti-neoplasm pharmaceutical agent or composition which constitutively produces IL-12, GM-CSF or CD and, optionally, includes a pharmaceutically acceptable carrier or diluent. The anti-tumor agent according to the present invention can be administered by any number of means and routes known in the art. For example, administration may be by subcutaneous, intravenous, intrathecal, intraventricular, intra-arterial, intramuscular, or intraperitoneal injection, by infusion, or preferably, by direct intratumoral injection. The dosage administered will be dependent upon the condition of the patient and the severity of the disease. Anti-tumor compositions comprising $10^4$ to $10^9$ virus, preferably $10^7$ to $10^8$ virus, at a dose, are administered to a patient according to the invention. The treatment can comprise several doses at spaced apart intervals, according to the necessity.

The recombinant HSV expressing IL-12 or other anti-cancer/anti-tumor agent according to the invention will be used in a method for the treatment of a patient or subject suffering from cancer, e.g., a malignant solid tumor, lymphoma or leukemia. The method of treatment includes the step of administering a therapeutically effective amount of an HSV vector expressing an IL-12 or other anti-cancer product encoding nucleic acid sequence into a patient or subject such that an anti-tumor response is induced in the subject.

The terms "patient" and/or "subject" as used herein mean all animals including humans. Examples of patients and/or subjects include humans, rodents, and monkeys.

A "therapeutically effective amount" is an amount of a HSV vector expressing IL-12 or other anti-tumor/cancer agent, that when administered to a patient or subject, inhibits tumor growth, causes tumor regression, prevents metastasis or spread of the tumor, prolongs the survival of the subject or patient, and combinations thereof.

The anti-tumor agents of the present invention can be administered to a patient or subject either alone or as part of a pharmaceutical composition of the agents admixed with a pharmaceutically acceptable carrier, diluent, or excipient.

A preferred route of administration is direct, intratumoral injection. Compositions suitable for injection may comprise physiological acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifing, and dispensing agents. Prevention of the action of microorganisms can be controlled by addition of any of various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

The invention will now be illustrated by the following examples without limiting thereto. In the examples the following Experimental Methods were employed:

Experimental

Materials and Methods

Cells. Vero cells (American Type Culture Collection [ATTC], Rockville, Md.) were grown and maintained in Minimal Essential Medium (Cellgro, Mediatech) containing 7% fetal bovine serum. The human 143 thymidine kinase minus cells (143tk–, ATCC) were grown in Dulbecco's modified Eagle's medium (DMEM) (Cellgro) supplemented with 10% fetal bovine serum. Rabbit skin cells (originally acquired from Dr. J. McClaren, University of New Mexico, Albuquerque, N.Mex., USA) were maintained in DMEM supplemented with 5% fetal bovine serum. The human malignant glioma cell lines U251MG and D54MG were obtained from D. D. Bigner (Duke University, Durham, N.C., USA) while the murine neuroblastoma cell line Neuro-2A (derived from stain A/J mice) was purchased from the ATCC (CCL 131, passage 171). These latter three cell lines were maintained in a 50:50 mixture of DMEM and Ham's Nutrient Mixture F-12 (DMEM/F12) supplemented to 2.6 mM L-glutamine and 7% FBS.

Plasmids and viruses. HSV-1 (F) strain is a low passage clinical isolate used as the prototype HSV-1 strain in our series (Post et al. (1981) Cell 25, 227–232; Jenkins et al. (1986) J. Virol. 59, 494–9). Viruses R3616 and R4009, which contain a 1 kb deletion and a stop codon, respectively, within both copies of the $\gamma_1 34.5$ gene, have been described previously (Chou et al. (1990) Science 250, 1262–1266). Construction of M002, which expresses murine interleukin 12 (mIL-12) under the transcriptional control of the murine early-growth response-1 promoter (Egr-1), is described below. This strategy is identical to that used to construct the cytokine-expressing viruses R8306 (mIL-4) and R8308 (mIL-10) (Andreansky et al. (1998) *Gene Ther.* 5, 121–130). The plasmids containing the p40 and p35 subunits of mIL-12 in pBluescript-SK+ (Stratagene) (Schoenhaut et al. (1992) *J. Immunol.* 148, 3433–3440), were kindly provided by Dr. Ueli Gubler (Hoffman-LaRoche, Inc., Nutley, N.J., USA). The p40 subunit was removed by digestion with HindIII (5' end) and BamHI (3' end) and the p35 subunit was removed by digestion with NcoI (5' end) and EcoRI (3' end). The internal ribosome entry site, or IRES, sequence was amplified from vector pCITE-4a+ (Novagen, Madison, Wis.) using polymerase chain reaction (PCR) and primers 5'-CITE (5'-CGCGGATCCTTATTTTCCACCATATTGCC-3') (SEQ ID No: 1), which has a BamHI site, and 3'-CITE (5'-GGAGCCATGGATTATCATCGTGTTTTTC-3') (SEQ ID No: 2), which has an NcoI site that retains the translational start sequence. Plasmid pBS-IL12 was constructed by three-way ligation of the murine p40, murine p35 and IRES sequences into HindIII and EcoRI sites of pBS-SK+ such that the IRES sequence separates the p40 and p35 coding sequences. This effectively duplicates a strategy previously reported for expression of the mIL-12 subunits (Tahara et al. (1995) *J. Immunol.* 154, 6466–6474). The IL-12 genes were entirely sequenced by the University of Alabama at Birmingham Cancer Center DNA Sequencing Facility.

The HSV shuttle plasmid pRB4878 has been previously described (Andreansky et al. (1998) *Gene Ther.* 5, 121–130). Plasmid 4878-IL12 was constructed as follows: pBS-mIL-12 was digested with XhoI and SpeI to remove a 2.2 kb fragment containing the entire IL-12 subunit coding regions, including the IRES, ends filled in using the Klenow fragment, and ligated into a blunted KpnI site located between the Egr-1 promoter (a mammalian promoter) and hepatitis B virus polyA sequences within pRB4878. M001 (tk-) and M002 (tk repaired at native locus) were constructed via homologous recombination as described previously (Andreansky et al. (1998) *Gene Ther.* 5, 121–130). Two tk-repaired viruses M002.29 and M002.211, were confirmed by Southern blot hybridization of restriction enzyme-digested viral DNAs which were electrophoretically separated on a 1% agarose, 1xTPE gel and transferred to a Zeta-Probe membrane (Bio-Rad). The blot was hybridized with the appropriate DNA probe labeled with alkaline phosphatase using the Gene Images AlkPhos Direct DNA labeling system (Amersham-Pharmacia Biotech, Piscataway, N.J.). IL-12 production was demonstrated by enzyme-linked immunosorbent assay (ELISA).

ELISA. Production of murine IL-12 by M002 was confirmed and quantified using a murine p70 ELISA kit (R&D Systems, Minneapolis, Minn.). Briefly, six well plates were seeded at a confluency of $4\times10^5$ cells/well one day prior to infection with M002 or control virus at a multiplicity of infection (M.O.I.)=1 in a total volume of 0.5 ml. After two hours, the inoculum was removed, 1 ml of growth medium was overlaid onto infected wells and plates incubated 24 hr at 37° C. The supernatant was removed, transferred to microcentrifuge tubes, and spun down briefly to remove cellular debris. Either undiluted or 10-fold dilutions of supernatants were analyzed by ELISA, according to the manufacturer's protocol. Experiments were performed at least three separate times to determine average level of cytokine production.

In vitro characterization of M001/M002. In vitro replication of M001 in subconfluent cultures of the human malignant glioma cell lines U251MG and D54MG was determined, as previously described (Andreansky et al. (1998) *Gene Ther.* 5, 121–130), at 12, 24, 48 and 72 hours post-infection hpi). For cytotoxicity assays, monolayers U251MG and D54MG cells, as well as the murine neuroblastoma cell line Neuro-2A were infected with M002.29 and M002.211 at an M.O.I.=1. The $TD_{50}$ was determined by alamarBlue™ assay, as described (Andreansky et al. (1997) *Cancer Res.* 57, 1502–1509). Dye conversion values were obtained by reading plates on a Bio-Tek EL310 plate reader (Winooski, Vt.) with the O.D. value at 590 nm subtracted from the O.D. at 562 nm. The decrease in O.D. relative to uninfected cells was plotted against number of virus plaque forming units (pfu)/ml to determine the number of pfu needed to produce a 50% reduction in O.D.

Animals. Specific pathogen-free female A/J strain mice were obtained from Charles River Laboratories and used at approximately eight weeks of age. All animal studies were conducted in accordance with guidelines for animal use and care established by The University of Alabama at Birmingham Animal Resource Program and the Institutional Animal Care and Use Committee (IACUC protocol 97K03985).

In vivo characterization of M002. For determination of M002 neurovirulence in A/J strain mice, graded numbers of virus pfu were prepared in sterile milk and 5 µl of each dilution were inoculated into the right cerebral hemisphere of 3–10 mice as described (Chambers et al. (1995) *Proc. Natl. Acad. Sci. USA* 92, 1411–1415). For survival studies, A/J strain mice were stereotactically inoculated with $10^5$ Neuro-2A cells in the right cerebral hemisphere. Five days later, mice were randomly divided into three cohorts and $5\times10^6$ pfu of M002, R3659 or vehicle were stereotactically inoculated into each tumor. Mice were assessed daily; moribund mice were sacrificed and the date of death recorded as described (Chambers et al. (1995) *Proc. Natl. Acad. Sci. USA* 92, 1411–1415).

Histopathology. Three sets of three mice each were injected with Neuro-2A, then treated with M002, R3659 or vehicle as described in the survival experiment. At days three and seven, one mouse from each group was sacrificed and its brain harvested and frozen in Tissue-Tek OCT compound. Sections 10–12 microns thick were cut through the injection site in each brain and mounted on TEPSA-coated slides, fixed in 95% ethanol and blocked in PBS-2% BSA. Sections were stained with standard hemotoxylin and eosin to determine degree of residual tumor, presence of neurotoxicity and extent of any inflammatory response. To characterize the nature of the inflammatory infiltrate, serial sections were reacted with rat monoclonal antibodies specific for mouse CD4, CD8, and macrophage markers and the antibody binding detected using biotinylated rabbit anti-rat Ig followed successively with an avidin-biotin-horseradish peroxidase complex and 1% diaminobenzidine (Andreansky et al. (1998) *Gene Ther.* 5, 121–130).

Results

Construction of a recombinant HSV-1 expressing murine IL-12. Previously, work by Applicants demonstrated that recombinant HSV which express murine interleukin-4 (IL-4) could significantly improve survival when injected into tumors implanted in brains of immunocompetent mice in a syngeneic murine model (Andreansky et al. (1998) *Gene Ther.* 5, 121–130). To extend these initial studies, Applicants evaluated recombinant HSV that would express the well-described anti-tumor cytokine IL-12.

Figure 1:
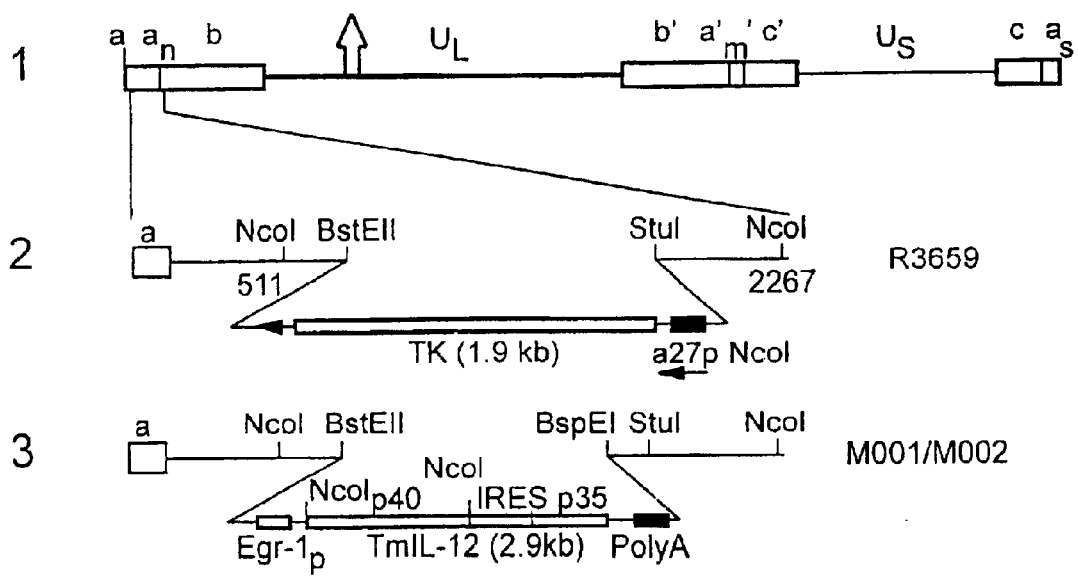
FIG. 1. Schematic representation of mIL 12-expressing HSV (M002). Line 1 illustrates the HSV-1 (F) Δ305 genome, which contains a 501 bp deletion within the tk gene, as indicated by the Δ symbol. $U_L$ and $U_S$ represent the unique long and unique short sequences, respectively. The inverted repeat sequences are indicated by a, b, and c, with subscripts n and m representing variable numbers of a sequences. Line 2 shows the sequence arrangement of the recombinant HSV R3659. The BstEII-StuI fragment within the $\gamma_1 34.5$ gene was replaced by the chimeric α27-tk gene in the inverted sequences ab (shown above) and b'a' (not shown) flanking the $U_L$ sequence. Line 3 shows the sequence arrangements of the relevant regions in the recombinant mIL 12-expressing HSV M001 (tk−) or M002 (tk+). NcoI restriction sites are indicated.

Biologically active mIL-12 consists of a heterodimer of the p40 and p35 subunits. Therefore, recombinant HSV M001(tk-) and M002 (tk+) were constructed to express both mIL-12 subunits within a single expression cassette, separated by the internal ribosome entry site (IRES) from the 5' untranslated region of equine encephalomyocarditis virus (FIG. 1). Recombinant virus M001 was obtained by co-transfection of plasmid DNAs with R3659 viral DNA and selection of tk(-) viruses on 143tk- cells overlaid with medium containing 100 µg/ml bromodeoxyuridine. The recombinant tk(-) mIL-12-expressing virus M001 was confirmed by Southern blot hybridization (data not shown).

Figure 2:
FIG. 2. Southern blot hybridization confirming presence of mIL-12 in M002. Viral DNAs were isolated, digested with NcoI, electrophoretically separated, and Southern blot hybridization performed as described in Materials and Methods. The predicted fragment sizes for each viral DNA (1.76 kb for HSV-1 (F), 0.7 kb for R3659, and 2.2 kb for M002) are indicated by arrows. The 1.6 kb, 0.52 kb and all smaller bands of the 1 kb DNA ladder (Life Technologies) will also hybridize to the probe, which has the same vector backbone as the ladder.

Recombinant virus M002 was obtained by cotransfection of M001 viral DNA with pRB4867, a plasmid used to repair the 501 bp deletion within the tk gene in its native locus ($U_L23$), and subsequent selection in HAT medium. These recombinant viruses contain two copies of the IL-12 construct replacing both copies of the $\gamma_1 34.5$ gene. To confirm the presence of the mIL-12 insert in M002, viral DNAs were isolated, digested with NcoI, and evaluated by Southern blot hybridization as described in Materials and Methods and shown in FIG. 2. Repair of the tk gene was also verified by hybridization to a probe specific for the tk gene insert (data not shown).

Expression of mIL-12 by M002. To determine if M002 expressed physiologically relevant levels of murine IL-12, culture supernates from M002- or R3659-infected Vero and Neuro2A cells were quantified using a commercially available ELISA kit specific for mIL-12 p70 heterodimers. Applicants evaluated IL-12 production from two genetically identical subclones of M002, clone 29 and clone 211. The averaged values are indicated in Table 1. The highest production of mIL-12 by M002 was seen in Vero and Neuro-2A cells, which produced 3–4 ng/$5 \times 10^5$ cells/24 hours after infection at an MOI=1. Production was slightly lower in the D54MG and U251MG cell lines, at 1.8 and 0.8 ng/$5 \times 10^5$ cells/24 hours. Such levels are physiologically relevant and have been shown to produce anti-tumor responses in other models (Toda et al. (1998) *J. Immunol.* 160, 4457–4464; Zitvogel et al. (1994) *Hum. Gene Ther.* 5, 1493–1506).

TABLE 1

IL-12 production* by M002 in normal and tumor cell lines cytokine production (pg/ml/24 h)

| Vero | D54MG | U251MG | Neuro2A |
|---|---|---|---|
| 3400 | 1780 | 820 | 3240 |

*Values indicated represent only mIL-12 heterodimers.

Figure 3A:
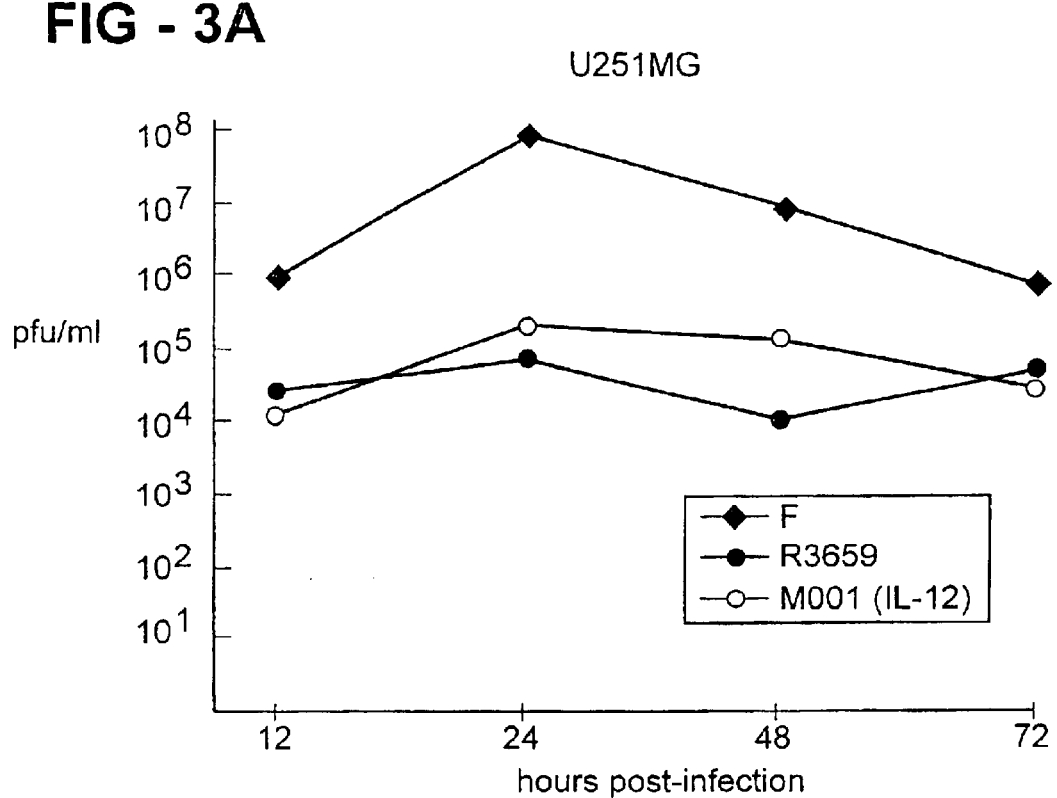
FIG. 3. In vitro replication of M001 in human glioma cells. Replicating monolayers of U251MG (top) or D54MG (bottom) human malignant glioma cell lines were infected at 1 pfu/cell with either HSV-1 (F) (closed diamonds), R3659 (closed circles) or M001 (open circles). Replicate cultures were harvested at 12, 24, 48 and 72 hours post-infection and virus titers determined on Vero cell monolayers.
Figure 3B:
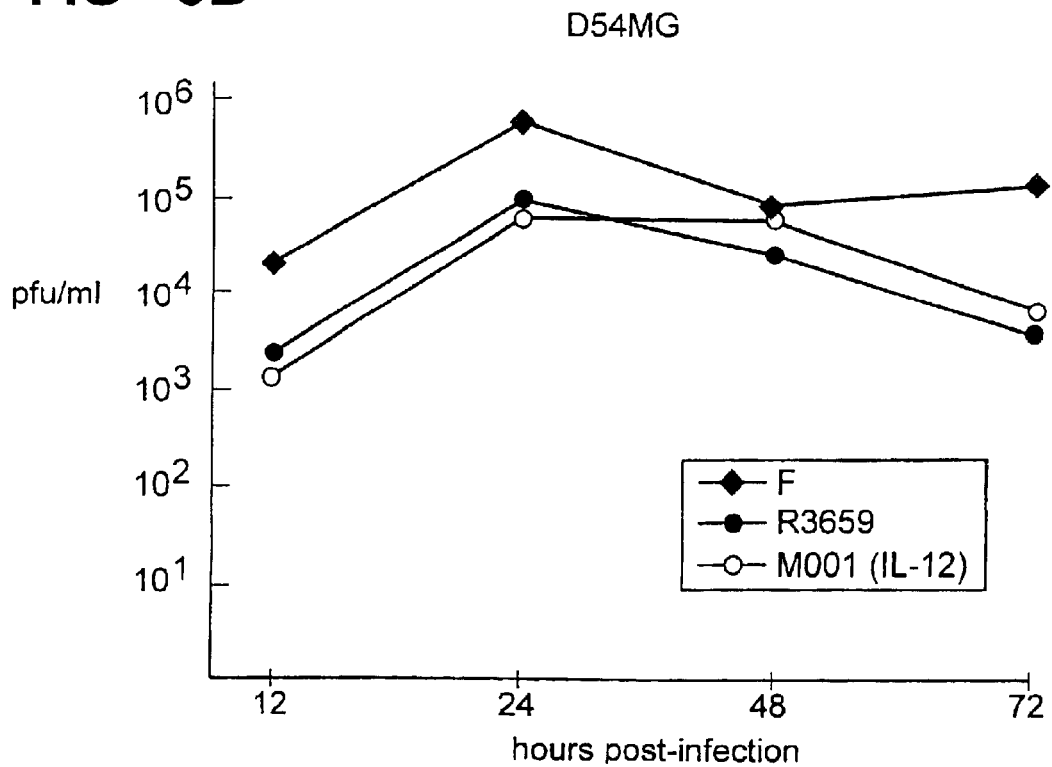

Growth of wild-type and recombinant viruses in tumor cell lines. Before repairing the tk gene to create M002, Applicants first established the replication competence of our tk(−) IL-12 expressing HSV (M001) as compared with wild-type "F" or the backbone virus R3659, in the human glioma cell lines D54MG and U251MG. As indicated in FIG. 3, M001 replicated as well as R3659 in both glioma cell lines, and as well as the wild-type "F" strain in D54MG. This confirmed that replication competence of the IL-12 expressing virus remained intact and would be suitable for comparisons with other cytokine-expressing or parent viruses.

Viruses containing mutations or deletions within the $\gamma_1 34.5$ locus have previously been shown to have a direct cytolytic effect on D54MG and U251MG (Andreansky et al. (1997) *Cancer Res.* 57, 1502–1509). Applicants quantitatively measured the cytolytic activity of M002 on Neuro2A cells, as well as D54MG and U251MG, by alamarBlue™ assay and compared the results with cytolytic activity of the backbone virus, R3659. As shown in Table 2, the cytolytic activity of M002 was slightly higher than R3659 in all cell lines tested. Thus, this virus is at least as cytotoxic in both human glioma cells and in murine Neuro2A cells as its parent virus, and may even have a slight growth advantage.

TABLE 2

Viral cytotoxicity of tumor cell lines

| Cells | Tumor/Cell Origin | R3659 pfu/$TD_{50}$ | M002.29 pfu/$TD_{50}$ | M002.211 pfu/$TD_{50}$ |
|---|---|---|---|---|
| U251MG | GBM | 1.9 | 1 | 1.1 |
| D54MG | GBM | 14.4 | 1.6 | 7.8 |
| Neuro2A | Neuroblastoma | 3 | 2.6 | 5.6 |

Values were obtained 3 days after virus infection, and 3 hour incubation with alamarBlue ™ dye.

A syngeneic model for neuroblastoma. The GL-261 cell line is a murine glioma line derived from C57BL/6 mice, and are relatively resistant to infection by HSV-1 (Lopez (1975) *Nature* 258, 152–153). Thus, this syngeneic model is not the ideal system for evaluating the therapeutic potential of Applicants' recombinant cytokine-expressing HSV, which replicate much more efficiently in human cells than in GL-261 cells. Therefore, Applicants tested their cytokine-expressing viruses in a syngeneic model using a murine strain that would be more susceptible to HSV infection. Strain A/J mice were utilized due to their known sensitivity to HSV-1 (Lopez (1975) *Nature* 258, 152–153). There are currently no syngeneic glioma models in A/J mice. However, Neuro2A cells are a neuroblastoma cell line originally derived from A/J mice. Neuro2A tumors were established in brains of A/J mice to be evaluated as a syngeneic brain tumor model system in a more sensitive murine strain. To determine optimal tumor cell dose for evaluating M002 in these tumors in vivo, $1 \times 10^3$, $10^4$ or $10^5$ cells were stereotactically introduced into A/J strain mice as described in Materials and Methods, and followed to determine median survival rates for each dose. A dose-response effect was defined for survival, which ranged from 14 to 25 days. Based on this study, Applicants elected to inoculate between $5 \times 10^4$ and $1 \times 10^5$ cells to produce a median survival of three weeks from tumor induction in order to facilitate a rapid and stringent evaluation of the survival effects of the therapeutic viruses.

Neurovirulence. Previous studies with G207, a genetically-engineered HSV-1 currently in human trials for the treatment of malignant glioma, have shown no neurovirulence in this assay at doses of $10^7$ pfu. Thus, the maximum tolerated dose was determined (pfu/$LD_{50}$) for both clones of Applicants' IL-12 EL expressing virus, M002.29 and M002.211. For clone 211, up to $2 \times 10^7$ pfu of virus could be directly injected without adverse effects, whereas the maximum tolerated dose of clone 29 was $5 \times 10^6$ pfu (data not shown). Since clone 211 appeared to be the safer of the two, this virus was tested for experimental therapy of Neuro2A tumors, and is referred to herein as "M002."

Figure 4:
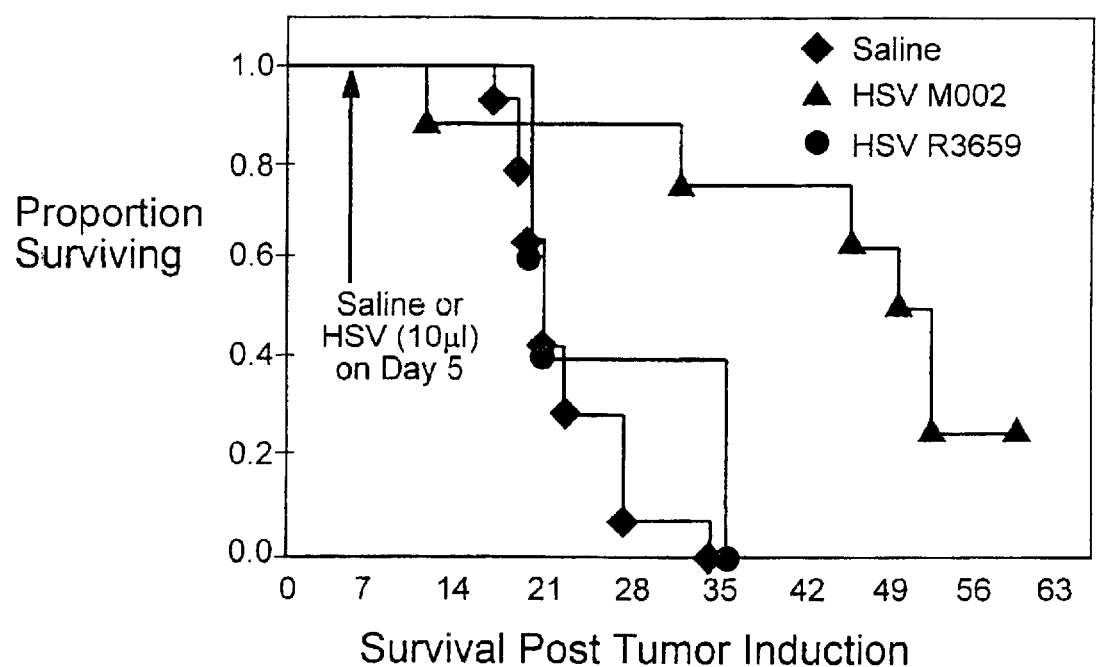
FIG. 4. Survival of A/J strain mice with intracerebral Neuro-2A neuroblastomas treated with M002. Neuro-2A cells ($1\times10^4$/5 μl) were injected intracerebrally in A/J mice. Five days later, intracerebral tumors were injected with 10 μl of saline or $2\times10^7$ pfu of HSV R3659 or HSV M002 and mouse survivals were monitored. Median survival for saline-treated mice was 19.8 days versus 50.5 days for M002 treated mice (p=0.002), and 19.5 days for HSV R3659-treated mice. Histologic examination of the brains of survivors killed at 59 days revealed no persistent tumor.
Figure 5:
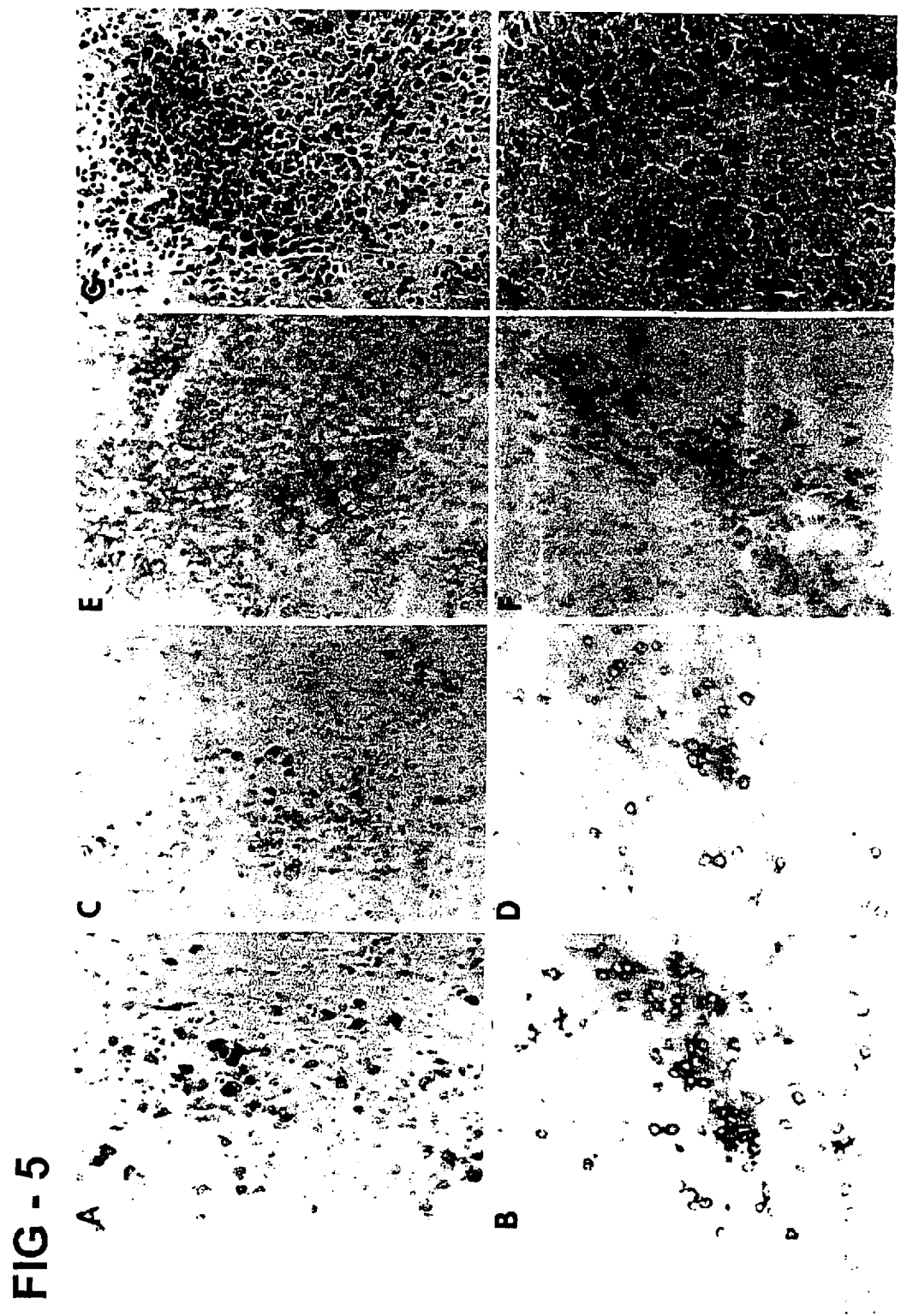
FIG. 5. Immunohistologic identification of inflammatory cell infiltrates. A/J female mice were injected intracerebrally with Neuro-2A cells ($1\times10^{5+}$/5 μl) and five days later were injected intratumorally with $1\times10^7$ pfu of HSV R3659 (Panels A, C, E, G) or HSV M002 (Panels B, D, F, H). Six days later, the mice were killed and their brains removed intact and embedded in OCT for preparation of frozen sections. Serial 10μ-thick sections were reacted with rat monoclonal antibodies to CD4+ (Panels A, B) or CD8+ T (Panels C, D) cells or macrophages (Panels E, F) and antibody binding detected using horseradish peroxidase-labeled anti-rat antibody and sections were counterstained with Mayer's hematoxylin. Hematoxylin-eosin stained adjacent sections were also shown (Panels G, H).

Survival of A/J strain mice with intracerebral Neuro-2A neuroblastomas treated wit M002. To evaluate the sensitivity of Neuro2A tumors to HSV infection in A/J strain mice, $1 \times 10^4$ tumor cells were injected intracranially into A/J female mice followed five days later by intratumoral injection of $1 \times 10^7$ pfu (in 5 μl) of either R3659 or M002 (mIL-12). As a control, 5 μl of the diluent were also injected. Data shown in FIG. 4 represent a composite of three experiments, the median survival post-tumor induction in mice injected with diluent only was 19.8 days, and all animals were dead by day 34. In contrast, mice with M002-injected tumors had a significant increase on median survival of 50.5 days (p=0.00023), calculated using the log-rank test. Mice that received an intratumoral injection of R3659 had a median survival (19.5 days) that was not significantly different (p=0.556) from vehicle-treated mice. All survivors were sacrificed at 59 days and their brains examined histologically but there was no evidence of tumor.

Immunohistologic identification of inflammatory cell infiltrates. Intratumoral injection of the parent $\gamma_1 34.5^-$ HSV, R3659, induced a mild but discernible immune-related inflammatory response characterized principally by macrophages and $CD4^+$ T cells with a few $CD8^+$ T cells. These inflammatory cells were scattered throughout the tumor mass with occasional foci predominated by macrophages or $CD4^+$ T cells. In contrast, injection of M002 elicited a pronounced influx of macrophages and $CD4^+$ T cells with a significant increase in $CD8^+$ T cells as well. Inflammatory responses were maximal around days 5–6 and bad begun to regress by day 7 after viral injection.

Genetically engineered, neuroattenuated herpes simplex viruses (HSV) expressing various cytokines can improve survival in the treatment of experimental brain tumors. These attenuated viruses have both copies of $\gamma_1 34.5$ deleted.

Recently, Applicants demonstrated increased survival of C57BL/6 mice bearing syngeneic GL-261 gliomas when treated with an engineered HSV expressing IL-4, a potent mediator of $T_H$-2 type responses, as compared to treatment with the parent construct ($\gamma_1 34.5^-$) alone or a virus expressing IL-10 (*Gene Therapy* 5: 121, 1998). The construction of a conditionally replication competent mutant expressing both subunits of murine IL-12 (M002), and its evaluation in a syngeneic neuroblastoma murine model is described. IL-12 induces a $T_H$-1 type response, which may induce more durable anti-tumor effects. In vitro studies demonstrated that, when infected with M002, both Vero cells and Neuro2A neuroblastoma cells produced physiologically relevant levels of IL-12 heterodimers, as determined by ELISA. M002 was cytotoxic for human glioma cell lines U251MG and D54MG. Neurotoxicity studies, as defined by $pfu/LD_{50}$, performed in HSV-1 sensitive A/J strain mice revealed that M002 was not toxic even at high doses. When evaluated in an intracranial syngeneic neuroblastoma murine model, median survival of M002-treated animals was significantly longer than animals treated with R3659, the parent $\gamma_1 34.5^-$ mutant lacking any cytokine gene insert. Immunohistochemical analysis of M002-treated tumors revealed a pronounced influx of $CD4^+$ T cells and macrophages, as well as $CD8^+$ cells when compared with R3659-treated tumors. M002 produced a survival benefit via oncolytic effects combined with $T_H$-I mediated immunologic effects.

In view of the teaching presented herein, other modifications and variations of the present invention will readily be apparent to those of skill in the art. The discussion and description are illustrative of some embodiments of the present invention, but are not meant to be limitations on the practice thereof. It is the following claims, including all equivalents, which define the scope of the invention.

Any patents or publications mentioned in the specification are indicative of the levels of those skilled in the art to which the invention pertains. These patents and publications are herein incorporated by reference to the same extent as if each individual publication was specifically and individually indicated to be incorporated by reference.

SEQUENCE LISTING

<160> NUMBER OF SEQ ID NOS: 2

<210> SEQ ID NO 1
<211> LENGTH: 29
<212> TYPE: DNA
<213> ORGANISM: Artificial
<220> FEATURE:
<223> OTHER INFORMATION: primer

<400> SEQUENCE: 1
cgcggatcct tattttccac catattgcc                29

<210> SEQ ID NO 2
<211> LENGTH: 28
<212> TYPE: DNA
<213> ORGANISM: Artificial
<220> FEATURE:
<223> OTHER INFORMATION: primer

<400> SEQUENCE: 2
ggagccatgg attatcatcg tgttttte                 28

What is claimed is:

1. An anti-tumor pharmaceutical composition comprising a replication competent herpes simplex virus vector comprising a nucleic acid sequence encoding cytosine deaminase operatively linked to a promoter, and a pharmaceutically acceptable carrier.

2. A pharmaceutical composition according to claim 1, wherein said HSV vector is substantially aneurovirulent.

3. An anti-tumor pharmaceutical composition comprising a herpes simplex virus vector comprising a nucleic acid sequence encoding cytosine deaminase operatively linked to a promoter, and a pharmaceutically acceptable carrier, wherein the vector comprises a deletion of the $\gamma_1 34.5$ gene.

4. An anti-tumor pharmaceutical composition comprising a herpes simplex virus vector comprising a nucleic acid sequence encoding cytosine deaminase operatively linked to a promoter, and a pharmaceutically acceptable carrier, wherein the sequence is inserted within the $\gamma_1 34.5$ gene deletion.

5. A pharmaceutical composition according to claim 1, wherein the expression of the nucleic acid sequence encoding cytosine deaminase results in constitutive production of cytosine deaminase in vivo.

* * * * *